(12) United States Patent
Heiß-Chouquet et al.

(10) Patent No.: US 10,718,698 B2
(45) Date of Patent: Jul. 21, 2020

(54) BENDABLE AND/OR FOLDABLE ARTICLES AND METHOD OF PROVIDING BENDABLE AND/OR FOLDABLE ARTICLES

(71) Applicant: Schott AG, Mainz (DE)

(72) Inventors: Markus Heiß-Chouquet, Bischofsheim (DE); Matthias Jotz, Mainz (DE); Vanessa Hiller, Mainz (DE)

(73) Assignee: Schott AG, Mainz (DE)

( * ) Notice: Subject to any disclaimer, the term of this patent is extended or adjusted under 35 U.S.C. 154(b) by 19 days.

(21) Appl. No.: 16/119,437

(22) Filed: Aug. 31, 2018

(65) Prior Publication Data

US 2019/0072468 A1 Mar. 7, 2019

(30) Foreign Application Priority Data

Sep. 4, 2017 (DE) .................. 10 2017 120 320
May 2, 2018 (DE) .................. 10 2018 110 500

(51) Int. Cl.
*G01M 11/00* (2006.01)
*G01N 3/20* (2006.01)
(Continued)

(52) U.S. Cl.
CPC .............. *G01N 3/20* (2013.01); *G01M 11/08* (2013.01); *G02F 1/00* (2013.01); *G02F 1/1333* (2013.01);
(Continued)

(58) Field of Classification Search
CPC .... G02F 1/00; G02F 1/1333; G02F 1/133305; G02F 2001/13332; G02F 2001/133331;
H01L 33/48; H01L 51/0097; H01L 27/1218; G01N 33/386; G01N 33/388; G01N 2203/0003; G01N 2203/0026;
(Continued)

(56) References Cited

U.S. PATENT DOCUMENTS 4,075,886 A * 2/1978 Barker ..................... G01N 3/20
                                                      73/787
4,890,494 A * 1/1990 Osbond .................. G01N 27/18
                                                      73/335.01
(Continued)

FOREIGN PATENT DOCUMENTS

CN          105819684 A    8/2016
DE     10 2014 110 855 A1  2/2016
KR       10-2014-0063710   5/2014

OTHER PUBLICATIONS

B.R. Lawn and D.B. Marshall, "Hardness, Toughness, and Brittleness: An Indentation Analysis", Journal of the American Ceramic Society, 1979, vol. 62, No. 7-8, pp. 347-350 (4 pages).
(Continued)

*Primary Examiner* — Max H Noori
(74) *Attorney, Agent, or Firm* — Taylor IP, P.C.

(57) ABSTRACT

The present disclosure relates to bendable and/or foldable articles and uses thereof and to a method of providing bendable and/or foldable articles. The articles are of translucent and brittle material, such as glass, glass ceramic, ceramic or crystals. The articles may be used as a display cover such as a protecting cover in displays in, for example, smartphones, tablet computers, or TV devices. The articles may also be used as a substrate for electronic components, such as OLEDs or LEDs.

13 Claims, 5 Drawing Sheets

(51) Int. Cl.
| | |
|---|---|
| *G02F 1/1333* | (2006.01) |
| *G02F 1/00* | (2006.01) |
| *H01L 33/48* | (2010.01) |
| *H01L 51/00* | (2006.01) |
| *G01M 11/08* | (2006.01) |
| *H01L 27/12* | (2006.01) |
| *G01N 33/38* | (2006.01) |

(52) U.S. Cl.
CPC ........ *G02F 1/133305* (2013.01); *H01L 33/48* (2013.01); *H01L 51/0097* (2013.01); *G01N 33/386* (2013.01); *G01N 33/388* (2013.01); *G01N 2203/0003* (2013.01); *G01N 2203/0023* (2013.01); *G01N 2203/0075* (2013.01); *G01N 2203/0078* (2013.01); *G01N 2203/0098* (2013.01); *G01N 2203/0218* (2013.01); *G01N 2203/067* (2013.01); *G02F 2001/133302* (2013.01); *G02F 2001/133331* (2013.01); *H01L 27/1218* (2013.01)

(58) Field of Classification Search
CPC ... G01N 2203/0075; G01N 2203/0078; G01N 2203/0098; G01N 2203/0218; G01N 2203/067
USPC .......................................................... 73/788
See application file for complete search history.

(56) References Cited

U.S. PATENT DOCUMENTS 5,490,416 A * 2/1996 Adler ........................ G01N 3/42
73/82
9,321,677 B2 4/2016 Chang et al.

OTHER PUBLICATIONS

Jeetendra Sehgal and Setsuro Ito, "Brittleness of Glass" Journal of Non-Crystalline Solids 253, 1999, pp. 126-132 (7 pages).
"Standard Test Methods for Determination of Fracture Toughness of Advanced Ceramics at Ambient Temperature" described in ASTM International, ASTM-Norm C1421-15, p. 9 ff. (33 pages).
M. John Matthewson and Charles R. Kurkjian, "Strength Measurement of Optical Fibers by Bending", J. Am. Ceram. Soc., 69 [11], pp. 815-821, 1986 (7 pages).
Jeetendra Sehgal and Setsuro Ito, "A New Low-Brittleness Glass in the Soda-Lime-Silica Glass Family", J. Am. Ceram. Soc., 81 [9], pp. 2485-2488, 1998 (4 pages).
Japanese Office Action dated Sep. 26, 2019 for Japanese Patent Application No. 2018-164427 (5 pages).
Machine translation of Japanese Office Action dated Sep. 26, 2019 for Japanese Patent Application No. 2018-164427 (10 pages).
Korean Office Action dated Oct. 29, 2019 for Korean Patent Application No. 10-2018-0104566 (6 pages).
Machine translation of Korean Office Action dated Oct. 29, 2019 for Korean Patent Application No. 10-2018-0104566 (8 pages).

* cited by examiner

BENDABLE AND/OR FOLDABLE ARTICLES AND METHOD OF PROVIDING BENDABLE AND/OR FOLDABLE ARTICLES

BACKGROUND OF THE INVENTION

1. Field of the Invention

The present disclosure relates to bendable and/or foldable articles and uses thereof and to a method of providing bendable and/or foldable articles. The articles are of translucent and brittle material, such as glass, glass ceramic, ceramic or crystals. The articles may be used as display covers, such as protecting covers in displays as, for example, in smartphones, tablet computers, or TV devices. The articles may also be used as substrate for electronic components such as OLEDs or LEDs.

2. Description of the Related Art

Brittle material can be bent only until a certain limit of load. This limit is dependent on a number of material parameters and strength parameters. Current articles do not yet reach the requirements of customers with respect to desired bending radii.

The cases of loading that a bendable display is subjected to can be divided into three groups:
1) Tensile load due to bending;
2) Impact loads occurring, for example, due to dropping the product or dropping of objects onto the display; and
3) Load by scratching with, for example hard objects.

In the prior art, there are no articles with acceptable load properties. The load properties are dependent on a number of material parameters and strength parameters such as, for example, Young's modulus, Poisson's ratio, fracture toughness, compressive stress, characteristic penetration depth, thickness of the article, hardness, density, and properties at subcritical crack propagation. The influence of the various parameters on the load properties is complex. Moreover, there are diverse interrelations among the parameters. So far, an optimization of all parameters has not been achieved. It has neither been achieved so far to identify, out of the multitude of parameters, the ones that are particularly relevant for an improvement of the load properties. Furthermore, it would be desirable to not only have the particularly relevant parameters at hand, but also a relation between them that enables correlating the particularly relevant parameters and drawing conclusions from such correlation with respect to the load properties.

Thus, there is a need in the art to provide articles with increased life expectancy at bending load and a method of providing such articles. Increased life expectancy means that the articles resist the loads described herein longer, as compared to an article of the prior art. The increased bendability results in smaller radii being achieved without breakage. Thus, increased life expectancy also means that the article has a bendability to smaller radii before breakage, as compared to the prior art. There is also a need in the art to provide articles and methods for producing such articles, wherein a higher load (smaller bending radius) can be achieved with the articles at the same failure probability or the other way around, i.e., the failure probability is lower at a given load (bending radius). There is also a need in the art to provide articles with increased life expectancy at impact and/or scratching load, as well as a method for providing such articles. There is also a need in the art to provide articles and methods for their provision, wherein the articles have an increased life expectancy at load by bending and/or impact loads and/or scratching loads.

SUMMARY OF THE INVENTION

Some exemplary embodiments disclosed herein relate to a method of providing articles of translucent and brittle material with improved bending properties.

Some exemplary embodiments disclosed herein relate to a method of providing articles of translucent and brittle material, wherein the method comprises:
a) Determining the following parameters of individual articles of a plurality of articles:
   i. Fracture toughness $K_{Ic}$,
   ii. Compressive stress CS,
   iii. Characteristic penetration depth $x_c$, and
   iv. Thickness d of the article;
b) Selecting those articles of the plurality for which the following equation is satisfied:

$$\frac{395 \cdot K_{Ic}}{\sqrt{m}} = SP \cdot \left(\frac{\pi}{2} - \arcsin\left(\frac{B}{4 \cdot 10^{-6} \cdot m}\right)\right) - \frac{2}{d} \cdot \sqrt{(1{,}6 \cdot 10^{-11} \cdot m^2 - B^2)} +$$
$$CS \cdot \left(\left(1 - \frac{x_c}{0{,}843 \cdot d}\right) \cdot \left(\frac{\pi}{2} - \arcsin\left(\frac{B}{4 \cdot 10^{-6} \cdot m}\right)\right)\right) -$$
$$\frac{0{,}843 \cdot \sqrt{(1{,}6 \cdot 10^{-11} \cdot m^2 - B^2)}}{x_c}$$

wherein $$B = \frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right)$$

for $$0 \leq \frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right) \leq 4 \cdot 10^{-6},$$

wherein $B = 0$ for $$0 > \frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right),$$

wherein $B = 0$ for $$\frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right) > 4 \cdot 10^{-6},$$

wherein m=1 meter, wherein $x_c > 0$ μm, and wherein SP is larger than 250 MPa.

When using this equation, the lengths $x_c$ and d are applied in meter, the stresses CS and SP are applied in MPa and the fracture toughness $K_{Ic}$ is applied in MPa·√m. The numbers 395, 0.843, and 2.37 are dimensionless. Tensile stresses have to be applied as positive values and compressive stresses as negative values. CS is compressive stress and thus a negative number.

Determining the indicated parameters of fracture toughness $K_{Ic}$, compressive stress CS, characteristic penetration depth $x_c$, and article thickness d of individual articles does not necessarily have to be done directly on each individual article. Rather, determining the parameters of individual articles may, for example, also occur indirectly using one or more reference articles. In accordance with the present disclosure, it is possible to determine the parameters of individual article by determining the parameters using a reference article that allows conclusions with respect to the parameters of the individual articles. For example, regarding a production batch, it is possible not to determine one or more parameters directly on the selected articles but on one or more reference articles of the same batch, so long as the parameters are not different, or not substantially different, among individual articles of a batch. In this respect, "not substantial differences" are differences of at most 20%, such as at most 15%, at most 10%, at most 5%, at most 2%, or at most 1% between maximum and minimum values within one batch.

In some embodiments, the fracture toughness $K_{Ic}$ of individual articles is determined using one or more reference articles. The fracture toughness $K_{Ic}$ is well suited for such an indirect determination because the differences between individual articles are particularly small with respect to this parameter.

In some embodiments the disclosure relates to an article of translucent and brittle material with improved bending properties.

In some embodiments the disclosure relates to an article of translucent and brittle material, wherein the article has a fracture toughness $K_{Ic}$, a compressive stress CS, a characteristic penetration depth $x_c$ and an article thickness d, wherein the following equation is satisfied for the article:

$$\frac{395 \cdot K_{Ic}}{\sqrt{m}} = SP \cdot \left(\frac{\pi}{2} - \arcsin\left(\frac{B}{4 \cdot 10^{-6} \cdot m}\right)\right) - \frac{2}{d} \cdot \sqrt{(1{,}6 \cdot 10^{-11} \cdot m^2 - B^2)} +$$

$$CS \cdot \left(\left(1 - \frac{x_c}{0{,}843 \cdot d}\right) \cdot \left(\frac{\pi}{2} - \arcsin\left(\frac{B}{4 \cdot 10^{-6} \cdot m}\right)\right) - \frac{0{,}843 \cdot \sqrt{(1{,}6 \cdot 10^{-11} \cdot m^2 - B^2)}}{x_c}\right),$$

wherein $$B = \frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right)$$

for $$0 \leq \frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right) \leq 4 \cdot 10^{-6},$$

wherein $B = 0$ for $$0 > \frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right),$$

wherein $B = 0$ for $$\frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right) > 4 \cdot 10^{-6},$$

wherein m=1 meter, wherein $x_c > 0$ μm, and wherein SP is larger than 250 MPa.

The present disclose also relates to a set of n articles with the indicated properties. The article number n may be at least 2, 3, 4, 5, 10, 20, 50, or even at least 100. Such a "set of articles" includes articles that are spatially combined, specifically selected and provided for further use. In come embodiments, the "set of articles" does not include any articles that do not have the indicated properties, but only articles having the indicated properties. The term "set of articles" may also mean that the articles belonging to the set are spatially separated from potentially additionally present further articles that do not have the indicated properties and thus do not belong to the set of articles provided in accordance with the present disclosure. In some embodiments, the articles belonging to the set of articles originate from the same production batch.

Translucent material in the sense of the present disclosure may be material having a thickness of 2 mm, an internal transmission of electromagnetic radiation that is more than 25%, such as more than 60%, more than 80%, more than 90%, or more than 95% in a range of 50 nm in a range of 250 an, or within the spectral range of 380 to 800 nm.

Brittle material in the sense of the present disclosure may be material having a brittleness S of more than 0.1 $\mu m^{-1/2}$, such as more than 0.2 $\mu m^{-1/2}$, more than 0.5 $\mu m^{-1/2}$, more than 0.8 $\mu m^{-1/2}$, more than 1 $\mu m^{-1/2}$, more than 1.5 $\mu m^{-1/2}$, more than 2 $\mu m^{-1/2}$. In some embodiments, the brittleness S is at most 20 $\mu m^{-1/2}$, such as at most 18 $\mu m^{-1/2}$, at most 15 $\mu m^{-1/2}$, at most 12 $\mu m^{-1/2}$, at most 10 $\mu m^{-1/2}$, at most 9 $\mu m^{-1/2}$, at most 8 $\mu m^{-1/2}$. In some embodiments, the brittleness S is in a range of from 0.1 $\mu m^{-1/2}$ to 20 $\mu m^{-1/2}$, such as from 0.2 $\mu m^{-1/2}$ to 18 $\mu m^{-1/2}$, from 0.5 $\mu m^{-1/2}$ to 15 $\mu m^{-1/2}$, from 0.8 $\mu m^{-1/2}$ to 12 $\mu m^{-1/2}$, from 1 $\mu m^{-1/2}$ to 10 $\mu m^{-1/2}$, from 1.5 $\mu m^{-1/2}$ to 9 $\mu m^{-1/2}$, or from 2 $\mu m^{-1/2}$ to 8 $\mu m^{-1/2}$. Herein, brittleness S is given as the ratio of Vickers hardness H and fracture toughness $K_{Ic}$: $S = H/K_{Ic}$.

This ratio is used as a measure for brittleness as explained in Lawn, B. R.; Marshall D. B.; "Hardness, Toughness, and Brittleness: An Indentation Analysis"; Journal of the American Ceramic Society (1979). It is known how to determine the brittleness experimentally. The brittleness may be determined according to the explanations in Sehgal, J.; Ito, S.; "Brittleness of glass"; Journal of Non-Crystalline Solids (1999).

The translucent and brittle material may be selected from the group consisting of glass, glass ceramic, ceramic and crystals. Exemplary crystals are selected from the group consisting of sapphire, diamond, corundum, ruby, topaz, quartz and orthoclase; sapphire is the crystal in some embodiments. In some embodiments, the translucent and brittle material is a glass or a glass ceramic. In some embodiments the translucent and brittle material is a borosilicate glass, an aluminosilicate glass or an aluminoborosilicate glass. In some embodiments, the proportion of $Li_2O + Na_2O$ in the materials, such as in the composition of glasses, is more than 1 wt.-%, such as more than 3 wt.-% or more than 5 wt.-%. In some embodiments, the material, which may be a glass, contains $Na_2O$ but is free of $Li_2O$, $Rb_2O$ and $Cs_2O$. If it is indicated within the present description that materials, such as glasses, are free of a component or do not contain a component, this means that this component may only be present as impurity in the materials or glasses. This means that the component is not added or contained in substantial amounts. Non-substantial amounts in accordance with the present disclosure are amounts of less than 1000 ppm, such as less than 500 ppm or less than 100 ppm.

When brittle material is bent without further protecting measures, tensile stress is created at the convex surface, which causes breakage once a threshold value is exceeded. It has been found that particularly bendable and/or foldable articles are obtained if the parameters of fracture toughness $K_{Ic}$, compressive stress CS, characteristic penetration depth $x_c$ and article thickness d are selected such that a survival parameter SP of more than 250 MPa is obtained according to the previously described equation. SP has the dimension of a tensile stress and is given in MPa. Surprisingly it has also been found that an article of translucent and brittle material is particularly long-lived under bending load if the parameters fracture toughness $K_{Ic}$, compressive stress CS, characteristic penetration depth $x_c$ and article thickness d are in correlation with a survival parameter SP as described in the equation above, wherein SP is larger than 250 MPa. In some embodiments SP is at least 300 MPa, at least 350 MPa, at least 400 MPa, at least 450 MPa, at least 500 MPa, at least 600 MPa, at least 700 MPa, or at least 800 MPa. In some In some embodiments, SP is at most 1,000,000 MPa, at most 100,000 MPa, at most 20,000 MPa, at most 10,000 MPa, at most 7,500 MPa, at most 5,000 MPa, at most 4,000 MPa, at most 3,000 MPa, or at most 2,000 MPa. In some embodiments, SP is in a range of from >250 MPa to 1,000,000 MPa, such as from 300 MPa to 100,000 MPa, from 350 MPa to 20,000 MPa, from 400 MPa to 10,000 MPa, from 450 MPa to 7,500 MPa, from 500 MPa to 5,000 MPa, from 600 MPa to 4,000 MPa, from 700 MPa to 3,000 MPa, or from 800 MPa to 2,000 MPa.

An article produced in accordance with the present disclosure may be bendable and/or foldable around a bending axis. The bending axis may be arranged perpendicular to the longitudinal axis of the article. An article formed in accordance with the present disclosure may be bendable and/or foldable around a bending axis that is arranged perpendicular to the longitudinal axis of the article, wherein the article withstands 100,000 bending and/or folding events without breaking. An article formed in accordance with the present invention may be bendable and/or foldable around a bending axis that is arranged perpendicular to the longitudinal axis of the article, wherein the article withstands 200,000 bending and/or folding events without breaking. A bending and/or folding event may be that an article is bent and/or folded from a non-bent state to a bent state, wherein the bending radius is at most 20 mm, at most 10 mm, at most 5 mm or at most 2 mm. A bending axis being arranged perpendicular to the longitudinal axis of the article is particularly useful in case the article is used as a display cover, such as a protective cover in displays in, for example smartphones. The bending axis may be arranged such that bending and/or folding divides the article in essentially two equally sized parts. For example, a smartphone or another portable electronic device may be opened and closed like a book by bending and/or folding around such an axis.

It is known how to adjust fracture toughness KC, compressive stress CS, characteristic penetration depth $x_c$ and article thickness d. However, it was previously unknown that articles with excellent load properties can be obtained if the indicated parameters are selected such that they are in correlation with a survival parameter SP according to the previously described equation, wherein SP is larger than 250 MPa. The present disclosure thus enables the skilled person to obtain the articles having the excellent properties.

In accordance with the present disclosure, fracture toughness $K_{Ic}$ is to be understood as the fracture toughness under tensile load (Mode 1). This fracture toughness is given in MPa·√m and may be measured with the "Precracked-Beam-Method" described in ASTM-Norm C1421-15 (p. 9 ff.). The fracture toughness K may be determined using one or more reference articles. In some embodiments, the articles used for determination of the fracture toughness $K_{Ic}$ are not toughened, e.g. not chemically toughened. In some embodiments, $K_{Ic}$ is larger than 0.4 MPa·√m, such as at least 0.45 MPa·√m, at least 0.5 MPa·√m, at least 0.6 MPa·√m, at least 0.7 MPa·√m, or at least 0.8 MPa·√m. In some embodiments, $K_{Ic}$ is at most 100 MPa·√m, such as at most 75 MPa·√m, at most 50 MPa·√m, at most 10 MPa·√m, at most 8 MPa·√m, at most 5 MPa·√m. In some embodiments, $K_{Ic}$ is in a range of >0.4 MPa·√m to 100 MPa·√m, such as from 0.45 MPa·√m to 75 MPa·√m, from 0.5 MPa·√m to 50 MPa·√m, from 0.6 MPa·√m to 10 MPa·√m, 0.7 to 8 MPa·√m, or from 0.8 to 5 MPa·√m.

In order to further increase the lifetime at bending, the stress distribution in the article may also be changed. In some embodiments, the article is toughened, e.g., thermally and/or chemically toughened. For example, there is a possibility of chemically toughening articles, such as glass articles, by element exchange. Therein usually small alkali ions in the article are replaced by larger alkali ions. Typically, smaller sodium ions are replaced by larger potassium ions. However, it is also in accordance with the present disclosure that the very small lithium ions are replaced by sodium or potassium ions. It is also in accordance with the present disclosure that alkali ions are replaced by silver ions. A further possibility is that alkaline earth ions are exchanged for each other based on the same principle as described for alkali ions. Ion exchange between the article surface and a salt bath may take place in a bath of molten salt. Such a bath is also called a toughening bath. Pure salt melts such as, for example, molten $KNO_3$ may be used for the exchange. However, mixtures of salts or mixtures of salt and further components may be used as well. The survival probability of a bent article can be further increased if a specifically adjusted compressive stress profile is established within the article. This may be achieved by multi-step chemical exchange processes. A desired compressive stress profile may also be created by ion implantation.

By replacing small ions with large ions within the exchanged zone, a compressive stress is generated that, in a simple exchange process, decreases from the surface of the glass towards the center according to a complementary error function. The maximum compressive stress is just underneath the glass surface and is in the following indicated as CS (compressive stress). CS is a stress and is given in the unit MPa. CS may be measured with the measuring device commonly known as FSM-60LE produced by the company Orihara.

In some embodiments, CS is larger than 200 MPa, such as at least 400 MPa, at least 600 MPa, or at least 800 MPa. In some embodiments, CS is at most 20,000 MPa, such as at most 10,000 MPa, at most 5,000 MPa, at most 3,000 MPa. In some embodiments, CS is in a range of from >200 MPa to 20,000 MPa, such as from 400 MPa to 10,000 MPa, from 600 MPa to 5,000 MPa, or from 800 MPa to 3,000 MPa. The given values are the absolute values of CS. As described above, CS has to be used as a negative value in the equation disclosed herein.

The shape of the toughening profile at single-step element exchange is that of a complementary error function as described previously. The diffusion coefficient D is different for each ion species and for different temperatures, as well as for different materials. The diffusion coefficient D is measured in the unit $m^2/s$. Based on the diffusion coefficient D and the toughening time t, the characteristic penetration depth $x_c$ can be calculated as $x_c = 2 \cdot \sqrt{D \cdot t}$. The toughening time t is the time that the article is in the toughening bath. This time can be determined automatically or by manual time measurement. The diffusion coefficient D can be determined with a plurality of different methods in accordance with the present disclosure. The diffusion coefficient may be calculated using a depth profile of the exchanged ions after defined toughening temperature and time. This depth profile can for example, be measured by energy dispersive X-ray spectroscopy (EDX). Alternatively, the Time-of-Flight Secondary Ion Mass Spectrometry (ToF-SIMS) Method may be used. In the ToF-SIMS-Method, material is removed from the article surface using an ion beam and the composition of the thus created ions is measured. By removing material, it is "drilled" into the depth of the article and changes in the ion profile can be shown. Other suitable methods are also known.

Ions whose concentration is increased by the exchange process of chemical toughening in the exchanged zone, as compared to the basic material, are termed "exchanged ions" according to the present disclosure. The concentration of the exchanged ions decreases from the surface towards the interior of the article. Independent of the above-described equation $x_c = 2 \cdot \sqrt{D \cdot t}$, the characteristic penetration depth $x_c$ can also be determined as the depth, determined by the ion-depth-profile, which may be determined by, for example, ToF-SIMS or EDX, at which the ion concentration of the exchanged ions (such as K-ions) has decreased to 15.73% of the concentration difference between surface and basic material. This is because, after chemical toughening, the concentration of the exchanged ions decreases from the concentration at the surface to the concentration in the bulk according to a complementary error function:

$$c(x, t) = \mathrm{erfc}\left(\frac{x}{2 \cdot \sqrt{D \cdot t}}\right)$$

Thus, for x=xc:

$$c(x_c) = \mathrm{erfc}(1) \approx 15.73\%$$

Thus, in a depth of $x = x_c$, the proportion exceeding the basic proportion is approximately 15.73% of the maximum proportion at the surface.

Thus, the characteristic penetration depth $x_c$ is the depth in which the following is satisfied:

$$c_{ion}(x_c) = c_{ion}(\mathrm{bulk}) + 0.1573 \cdot (c_{ion}(\mathrm{surface}) - c_{ion}(\mathrm{bulk}))$$

In this equation, $c_{ion}(\mathrm{bulk})$ indicates the concentration of the exchanged ions in the basic material, $c_{ion}(\mathrm{surface})$ the concentration of the exchanged ions at the surface of the article and $c_{ion}(xc)$ the concentration of the exchanged ions in the depth $x_c$.

The surface of the articles of the present disclosure may be changed and/or removed, e.g., by etching and/or polishing, after toughening. The correlation of the equation of the present disclosure between fracture toughness $K_{Ic}$, compressive stress CS, characteristic penetration depth $x_c$ and article thickness d as well as the survival parameter SP is also satisfied if the surface of the article, such as a glass, is changed and/or removed, e.g., by etching and/or polishing. The following values are then used in the equation:
 the fracture toughness $K_{Ic}$ is determined as described above;
 the article thickness d is the thickness after the surface treatment;
 the compressive stress CS is the value of compressive stress at the surface after the surface treatment.

If the surface is changed after toughening, such as if a part of the exchanged surface is removed, e.g. by etching and/or polishing, the concentration of the exchanged ions at the surface is changed as well, for example by removal of surface parts having a particular high concentration of exchanged ions. Therefore, the characteristic penetration depth xc is determined according to the following and above-discussed equation as the depth in which the following is satisfied:

$$c_{ion}(x_c) = c_{ion}(\mathrm{bulk}) + 0.1573 \cdot (c_{ion}(\mathrm{surface}) - c_{ion}(\mathrm{bulk}))$$

In this equation, $c_{ion}(\mathrm{bulk})$ indicates the concentration of the exchanged ions in the basic material, $c_{ion}(\mathrm{surface})$ the concentration of the exchanged ions at the surface after the surface treatment and $c_{ion}(x_c)$ the concentration of the exchanged ions in the depth $x_c$.

The characteristic penetration depth $x_c$ has the unit of a length. In some embodiments, $x_c$ is at least 2 μm, such as at least 3 μm, at least 0.843*4 μm, at least 4 μm, at least 6 μm, at least 8 μm, or at least 10 μm. In some embodiments, $x_c$ is at most 50 μm, at most 30 μm, at most 27 μm, at most 25 μm, at most 24 μm, at most 22 μm, or at most 20 μm. In some embodiments, $x_c$ is in a range of from 2 μm to 50 μm, from 3 μm to 30 μm, from 0.843*4 μm to 27 μm, from 4 μm to 25 μm, from 6 μm to 24 μm, from 8 μm to 22 μm, or from 10 μm to 20 μm.

It has been found that it is useful if $x_c$ does not exceed certain extents in relation to the article thickness d. In some embodiments, $x_c$ is at most d/2, such as at most d/3, at most d/3.5, at most d/4, at most d/5, at most d/6, or at most d/7. However, in some embodiments $x_c$ is at least d/40, at least d/30, at least d/27, at least d/25, at least d/20, at least d/15, or at least d/10. In some embodiments, $x_c$ is in a range of from d/40 to d/2, from d/30 to d/3, from d/27 to d/3.5, from d/25 to d/4, from d/20 to d/5, from d/15 to d/6, or from d/10 to d/7.

In some embodiments, $x_c$ is at least 2 μm and at least d/40, such as at least 3 μm and at least d/30, at least 0.843*4 μm and at least d/27, at least 4 μm and at least d/25, at least 6 μm and at least d/20, at least 8 μm and at least d/15, at least 10 nm and at least d/10. In some embodiments, $x_c$ is at most 50 μm and at most d/2, at most 30 μm and at most d/3, at most 27 μm and at most d/3.5, at most 25 μm and at most d/4, at most 24 μm and at most d/5, at most 22 μm and at most d/6, or at most 20 μm and at most d/7.

The absolute extent of tensile stress at a given bending radius is approximately linearly proportional to the article thickness d. The higher the article thickness, the higher the bending stress. Bending stress means the tensile stress at the convex side of a bent article. The thickness of the article may be selected freely. The thickness is measured in the unit meter (m). In some embodiments, the article thickness d is at most 500 μm, at most 450 μm, at most 400 μm, or at most 300 μm. In some embodiments, the article thickness d is at least 5 μm, such as at least 20 μm, at least 50 μm, at least 100 m. In some embodiments, the article thickness d is in a range of from 5 μm to 500 μm, from 20 μm to 450 μm, from 50 μm to 400 μm, or from 100 μm to 300 μm. In some embodiments, the article thickness d is measured using a thickness caliper. It is also possible to calculate the article thickness via weight, basal area and density. Other suitable methods are possible as well.

Furthermore, it has been found that the tensile stress at the convex side of the article is approximately directly proportional to the Young's modulus of the translucent and brittle material. Therefore, it is useful for the lifetime of a bent article if the Young's modulus of the material is not very high. In some embodiments, the Young's modulus is at most 200 GPa, such as at most 150 GPa, at most 120 GPa, or at most 100 GPa. In some embodiments, the Young's modulus is at least 40 GPa, at least 50 GPa, at least 60 GPa, or at least 70 GPa. In some embodiments, the Young's modulus is in a range of from 40 GPa to 200 GPa, from 50 GPa to 150 GPa, from 60 GPa to 120 GPa, or from 70 GPa to 100 GPa. The Young's modulus may be determined using the speed of sound within the respective material. Determination of Young's modulus using the speed of sound is known.

The lifetime of a bent product can also be increased if the tensile stresses are shifted out of the article. This can be achieved in accordance with the present disclosure by applying a further material onto at least one side of the article, such as onto the side loaded with tensile stress. Therefore, the present disclosure also relates to a composite comprising an article formed in accordance with the present disclosure and a further material attached to at least one side of the article. It is sufficient to apply the further material onto the article edge and the proximity of the article edge. It is not necessary that the entire side of the article is provided with the further material. The "proximity of the article edge" may indicate the parts of a side of the article whose distance to the closest article edge in shortest connection is at least 10*d, and at most 50*d, such as at most 20*d, wherein "d" is the article thickness.

In some embodiments, the further material has a Young's modulus >10 GPa, such as at least 20 GPa, at least 50 GPa, at least 75 GPa, or at least 100 GPa. In some embodiments, the Young's modulus of the further material is at most 1,000 GPa, at most 800 GPa, at most 700 GPa, or at most 650 GPa. In some embodiments, the Young's modulus of the further material is in a range of from >10 GPa to 1,000 GPa, from 20 GPa to 800 GPa, from 50 GPa to 700 GPa, or from 100 GPa to 650 GPa.

In comparison to the Young's modulus of the article $E_{Article}$, the Young's modulus of the further material may be in a range of from $E_{Article}/10$ to $10*E_{Article}$, such as from $E_{Article}/5$ to $5*E_{Article}$, or from $E_{Article}/2$ to $2*E_{Article}$.

In some embodiments, the brittleness S of the further material is less than 20 $\mu m^{-1/2}$, such as less than 10 $\mu m^{-1/2}$, less than 5 $\mu m^{-1/2}$, less than 2 $\mu m^{-1/2}$, less than 1 $\mu m^{-1/2}$, less than 0.5 $\mu m^{-1/2}$, less than 0.25 $\mu m^{-1/2}$, less than 0.1 $\mu m^{-1/2}$, less than 0.05 $\mu m^{-1/2}$, or less than 0.005 $\mu m^{-1/2}$. In some embodiments, the thickness of the further material is in a range of from 0.2*d to 5*d, such as in a range of from 0.5*d to 2*d, wherein d is the thickness of the article. In some embodiments, the thickness of the further material is at least 10 $\mu m$, such as at least 50 $\mu m$, at least 100 $\mu m$, at least 200 $\mu m$, or at least 500 m. In some embodiments, the further material is selected from the group consisting of plastics, such as polymeric plastics, and metallic materials, such as metals. An exemplary plastic is polyethylene (PE). When the further material is a metallic material, the further material may be, for example, steel.

As described previously, tensile stresses may be shifted out of the article into the further material. Hence, it is useful if the further material has a comparably high offset yield point. In some embodiments, the 0.2% offset yield point of the further material, which may be a metallic material, is at least 50 N/mm², such as at least 75 N/mm², at least 100 N/mm², or at least 150 N/mm². The 0.2% offset yield point is the (uniaxial) mechanical stress at which the remaining strain after load relief with respect to the initial length of the sample is exactly 0.2%. The 0.2% offset yield point can be determined unambiguously from the nominal stress-total strain-curve.

It is also useful if the further material has a comparably high tensile strength. In some embodiments, the tensile strength of the further material, which may be a polymeric plastic, is at least 50 N/mm², at least 60 N/mm², at least 70 N/mm², or at least 80 N/mm². The tensile strength may be determined, for example, according to one of the following standards: EN ISO 6892-1, ISO 6892, ASTM E 8, ASTM E 21, DIN 50154, ISO 527, ASTM D 638.

Surprisingly, it has been furthermore found that geometrical effects in the article result in a decrease of the compressive stress at the article edges. The disadvantageous effect can be reduced by edge rounding. It has been surprisingly found in this respect that it is useful if the article thickness d, the characteristic penetration depth xc and the radius of rounding OVR have the following correlation: $d/3 > OVR > x_c/5$ In some embodiments, the radius of rounding OVR is less than d/3 and more than $x_c/5$. The radius of rounding OVR is measured on cross fractures of respective article sheets. Herein, OVR is the radius of the largest possible circle that can be fitted in the cross fracture to the corner of the cross fracture. The corner is therein the cross section at the edge of the original sheet. Measuring the OVR of individual articles may be done indirectly using one or more reference articles that allow conclusions regarding the OVR of the individual articles. For example, regarding a production batch, it is possible not to do the determination directly on the selected articles but on one or more reference articles of the same batch so long as the parameters are not different or not substantially different among individual articles of a batch. In this respect, "not substantial differences" are differences of at most 20%, such as at most 15%, at most 10%, at most 5%, at most 2%, or at most 1% between maximum and minimum values within one batch.

In some embodiments, the present disclosure relates to a method for providing articles of translucent and brittle material, wherein the radius of rounding OVR is determined and such articles are selected that have OVR less than d/3 and more than $x_c/5$ is. In some embodiments, the present disclosure relates to articles of translucent and brittle material, wherein the OVR is less than d/3 and more than $x_c/5$. In some embodiments, the present disclosure relates to a composite comprising an article of translucent and brittle material as well as a further material attached to at least one side of the article, wherein the OVR is less than d/3 and more than $x_c/5$.

For etching, an environment is used that is suitable for removal of the material. Hydrofluoric acid containing liquids such as ammonium bifluoride may be used in different concentrations. These can be used in mixtures with other liquids, such as with further acids. Concentrations and etching times can be adjusted with respect to the desired removal. In accordance with the present disclosure, etching can also be done with alkaline solutions. Etching with alkaline solutions requires longer etching times as compared to etching with HF. Exemplary alkaline solutions are potassium hydroxide solution (KOH) or sodium hydroxide solution (NaOH). Plasma etching may also be used in accordance with the present disclosure.

The efficiency of a compressive stress profile regarding the lifetime of a bent article can be shown using strength measurements of the respective glass. For this purpose, 2-point-bending measurements were made, wherein the strengths have been determined according to the publication of Matthewson und Kurkjian (J. Am. Ceram. Soc., 69 [11], pages 815-821 (1986)). Determination of strength of individual articles may be done indirectly using one or more reference articles that allow conclusions with respect to the strength of the individual articles. For example, regarding a production batch, it is possible not to do the determination directly on the selected articles but on one or more reference articles of the same batch so long as the parameters are not different or not substantially different among individual articles of a batch. In this respect, "not substantial differences" are differences of at most 20%, such as at most 15%, at most 10%, at most 5%, at most 2%, or at most 1% between maximum and minimum values within one batch.

It has been found that articles are particularly resistant against breakage at bending if there is a specific correlation between the mean values (MW) of the measurements series, the standard deviation (STABW) of the measurement series, the number N of samples in a measurement series and a strength parameter OFP that is calculated as follows:

$$OFP = 0.4 \cdot \exp\left(-\frac{N}{9}\right) + \frac{MW\left(1.3 - 0.25 \cdot \exp\left(-\frac{N}{8}\right)\right)}{STABW} - 0.5$$

In some embodiments, OFP is at least 2, such as more than 4. In some embodiments, OFP is at least 5, at least 10 or at least 20. In some embodiments, OFP is at most 100, such as at most 80, at most 70, or at most 60. In some embodiments, OFP is in a range of from >4 to 100, from 5 to 80, from 10 to 70, or from 20 to 60.

In some embodiments, the present disclosure relates to a method of providing articles of translucent and brittle material, wherein the strength parameter OFP is determined according to the above equation and such articles are selected at which OFP is more than 4. In some embodiments the present disclosure relates to articles of translucent and brittle material, wherein the strength parameter OFP is more than 4. In some embodiments the present disclosure relates to a composite comprising an article of translucent and brittle material as well as a further material attached to at least one side of the article, wherein the strength parameter OFP is more than 4. In some embodiments, OFP is at least 5, such as at least 10 or at least 20. In some embodiments, OFP is at most 100, such as at most 80, at most 70, or at most 60. In some embodiments, OFP is in a range of from >4 to 100, from 5 to 80, from 10 to 70, or from 20 to 60.

There may be subcritical crack growth in brittle materials. Therein, micro-defects become larger even at subcritical load, i.e., load that does not directly result in breakage, and may "grow up to" the critical range so that there is delayed breakage. Typically, the speed of crack growth is given as function of the relative stress intensity factor v, wherein an exponential correlation according to the following equation is apparent:

$$v = v_0 \left(\frac{K_I}{K_{Ic}}\right)^n$$

Surprisingly it has been found that, for a high life expectancy under constant tensile stress, the influence of air humidity is much more important than the exponent n that is a material parameter and is also indicated as n-value. It has been found that, in particular, such articles are suitable for use as bent articles in which the pre-factor $v_0$ in the above-given equation varies widely at variation of relative humidity in the range of between 20% rH and 70% rH. In some embodiments, the pre-factor $v_0$ varies at variation of the relative humidity in a range of between 20% rH and 70% rH by a factor of more than 15, such as more than 20, more than 25, more than 30, or more than 50.

In some embodiments, the present disclosure relates to a method of providing articles of translucent and brittle material, wherein such articles are selected at which the pre-factor $v_0$ varies at variation of relative humidity in the range of between 20% rH and 70% rH by a factor of more than 15, such as more than 20, more than 25, more than 30, or more than 50. In some embodiments, the present disclosure relates to articles of translucent and brittle material, wherein the pre-factor $v_0$ varies at variation of relative humidity in the range of between 20% rH and 70% rH by a factor of more than 15, such more than 20, more than 25, more than 30, or more than 50. In some embodiments the present disclosure relates to a composite comprising an article of translucent and brittle material as well as a further material attached to at least one side of the article, wherein the pre-factor $v_0$ varies at variation of relative humidity in a range of between 20% rH and 70% rH by a factor of more than 15, such as more than 20, more than 25, more than 30, or more than 50.

At impact load, there is a very local excessive stress increase that is composed of a compressive load in the center of the impact and tensile load at the edges. Therein the article has to absorb as usual the two components energy B and momentum p of the hitting object. The energy is absorbed by $$E = \int_0^m F(x) \cdot dx$$

whereas the momentum has to be absorbed by $$p = \int_0^{t_{contact}} F(t) \cdot dt$$

Therein x indicates the deflection of the article and m is the maximal deflection of the article, thus the path on which the energy is absorbed. Time is indicated by t and $t_{contact}$ indicates the contact time between the article and the hitting object. F(x) indicates the force on the hitting object at a deflection of x. F(t) is the force on the hitting object at the time point t. If applicable, the double momentum has to be transferred with respect to spring-back hitting objects. As can be seen from the equations, for both components the deflection during contact is highly important. If the same assembly with the same stiffness is looked at for different articles, different material parameters are important for the survival probability.

The crack-initiation-load describes the resistance of articles against crack formation upon penetration of an object. The crack-initiation-load essentially corresponds to the case resulting from impact load. Accordingly, a comparably high crack-initiation load is useful. In some embodiments, the crack-initiation-load of the article at 50% relative humidity is at least 1.5 N, such as at least 3 N, at least 5 N, or at least 10 N. In some embodiments, the crack-initiation-load of the article at 50% relative humidity is at most 200 N, such as at most 150 N, at most 75 N, at most 65 N, at most 55 N, at most 45 N, or at most 30 N. In some embodiments, the crack-initiation-load is in a range of from 1.5 N to 200 N, from 3 N to 150 N, from 5 N to 75 N, or from 10 N to 30 N. The crack-initiation-load may be determined with a Vickers indenter, as described by Sehgal and Ito (J. Am. Ceram. Soc., 81 [9], pages 2485-2488 (1998)).

A further point that is important with respect to impact load is the critical compression, which is the limiting compressive stress that a material tolerates before it has a disposition to cracks. This quantity corresponds to a strain and is dimensionless. In some embodiments, the critical compression of the article is at least 8%, such as at least 10%. The critical compression can be determined using cylinder compression. The article sample to be investigated may be put between the front surfaces of two cylinders so that pressure can be applied by the cylinders. A universal testing machine, for example of type INSTRON 6025, can be used for applying the pressure forces.

The Young's modulus E and the fracture toughness $K_{Ic}$ are important with regard to the strength against impact loads as well. The maximum pressure load of an article at a given geometry of the hitting tool is proportional to $$\frac{K_{Ic}^2}{E}.$$

Accordingly, a high fracture toughness $K_{Ic}$ and a small Young's modulus are useful. In some embodiments, $K_{Ic}$ is more than 0.4 MPa·√m such as at least 0.45 MPa·√m, at least 0.5 MPa·√m, at least 0.6 MPa·√m, at least 0.7 MPa·√m, or at least 0.8 MPa·√m. In some embodiments, the Young's modulus is at most 200 GPa, such as at most 150 GPa, at most 120 GPa, or at most 100 GPa.

During scratching, a hard material is moved over the glass surface or pushed into it. On the one hand, this causes unsightly scratches resulting from chippings and plastic deformations. On the other hand, cracks may be generated that reach into the depth of the article and may cause destruction of the article. Scratching of an article can be counteracted in several ways.

It is useful if the translucent and brittle material is hard. Surprisingly, it was found that it is not the Vickers hardness, but the Martens hardness, that is important. The Vickers hardness (for example of glasses) is known as a general hardness parameter, for example for determination of the brittleness. With respect to the Vickers hardness, a pyramid-shaped diamond is pushed into the glass and the indentation remaining after load relief is measured geometrically. The hardness is determined therefrom. This hardness is therefore a measure for the plastic deformation of a material. In contrast, for determination of the Martens hardness, the penetration depth or the contact area at a given tracking force are measured, respectively. Thus, this hardness provides information about the elastic deformation of the material. It has been surprisingly found that the Martens hardness is a better measure for the resistance of the glass because, during its determination, the stress conditions underneath the indenter are much more similar to those at load of the article. Breakage of an article, such as a glass, namely occurs (in particular at impact load) during load.

In some embodiments, the Martens hardness of the material is at least 1,000 MPa, such as at least 1,200 MPa, at least 1,500 MPa, at least 2,000 MPa. In some embodiments, the Martens hardness is at most 30,000 MPa, such as at most 25,000 MPa, at most 20,000 MPa, or at most 16,000 MPa. The Martens hardness may be determined according to DIN EN ISO 14577.

Furthermore, it has been found that it is useful if CS is comparably high. Thereby deep cracks can be avoided. In some embodiments, CS is more than 200 MPa such as CS is at least 400 MPa, at least 600 MPa, or at least 800 MPa.

It is also useful if the characteristic penetration depth $x_c$ is large because thereby a crack into the so-called "center-tension" can be avoided also at slightly deeper cracks so that the also slightly deeper cracks do not lead to breakage of the sheet. In some embodiments, $x_c$ is at least 2 µm, such as at least 3 µm, at least 4 µm, at least 6 µm, at least 8 µm, or at least 10 µm.

The present disclosure also relates to the use of an article or composite as a display cover, such as for smartphones, tablet computers, and/or TV devices.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

A plurality of articles of different production batches are provided. Fracture toughness $K_{Ic}$, compressive stress CS, characteristic penetration depth $x_c$ and article thickness d of the individual articles are determined. The determination of the indicated parameters of the individual articles is done for each production batch using ten reference articles, which are representative for the respective batch. Based on the determination of the parameters, those articles are selected for which the following equation is satisfied:

$$\frac{395 \cdot K_{Ic}}{\sqrt{m}} = SP \cdot \left(\frac{\pi}{2} - \arcsin\left(\frac{B}{4 \cdot 10^{-6} \cdot m}\right)\right) - \frac{2}{d} \cdot \sqrt{(1{,}6 \cdot 10^{-11} \cdot m^2 - B^2)} +$$

$$CS \cdot \left(\left(1 - \frac{x_c}{0{,}843 \cdot d}\right) \cdot \left(\frac{\pi}{2} - \arcsin\left(\frac{B}{4 \cdot 10^{-6} \cdot m}\right)\right)\right) -$$

$$\frac{0{,}843 \cdot \sqrt{(1{,}6 \cdot 10^{-11} \cdot m^2 - B^2)}}{x_c},$$

wherein

-continued $$B = \frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right)$$

for $$0 \le \frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right) \le 4 \cdot 10^{-6},$$

wherein $B = 0$ for $$0 > \frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right),$$

wherein $B = 0$ for $$\frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right) > 4 \cdot 10^{-6},$$

wherein m=1 meter, wherein $x_c > 0$ μm, and wherein SP is larger than 250 MPa.

In particular, those articles are not selected for which SP is not larger than 250 MPa. The selected articles are separated from the remaining articles and put together as a set of articles in accordance with the present disclosure.

Surprisingly, it was found that glass having a higher SP can be bent to a lower bending radius before it breaks.

Figure 1:
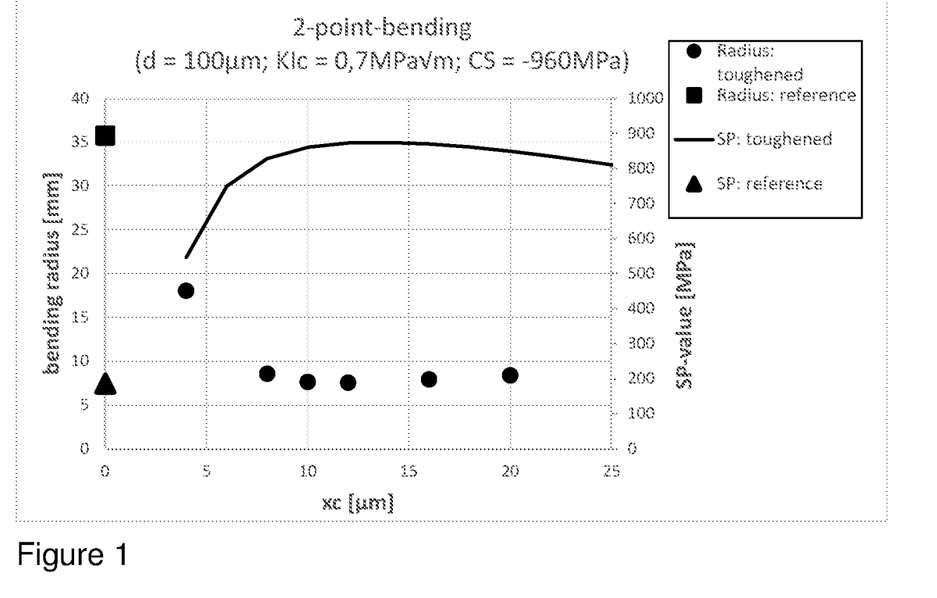
FIG. 1 illustrates the correlation between measured bending radii (characteristic value according to Weibull statistics) and the calculated SP-values (secondary y-axis) using an exemplary glass with d=100 µm, $K_{Ic}$=0.7 MPa·√m and CS=−960 MPa; the two reference values indicate the bending radius or the SP-value of a non-toughened glass, respectively.

FIG. 1 illustrates the correlation between measured bending radii (characteristic value according to Weibull statistics) and the calculated SP-values (secondary y-axis) using an exemplary glass. The two reference values indicate the bending radius or the SP-value of a non-toughened glass, respectively. It can be seen that the SP-value is highest for the lowest bending radii. This means that low bending radii can be achieved at high SP-values. It was measured using 2-point-bending. (see also Matthewson and Kurkjian (J. Am. Ceram. Soc., 69 [11], pages 815-821 (1986))). In this diagram, half of the distance of the plates at breakage of the glass was set as bending radius of the 2-point-bending.

Figure 2:
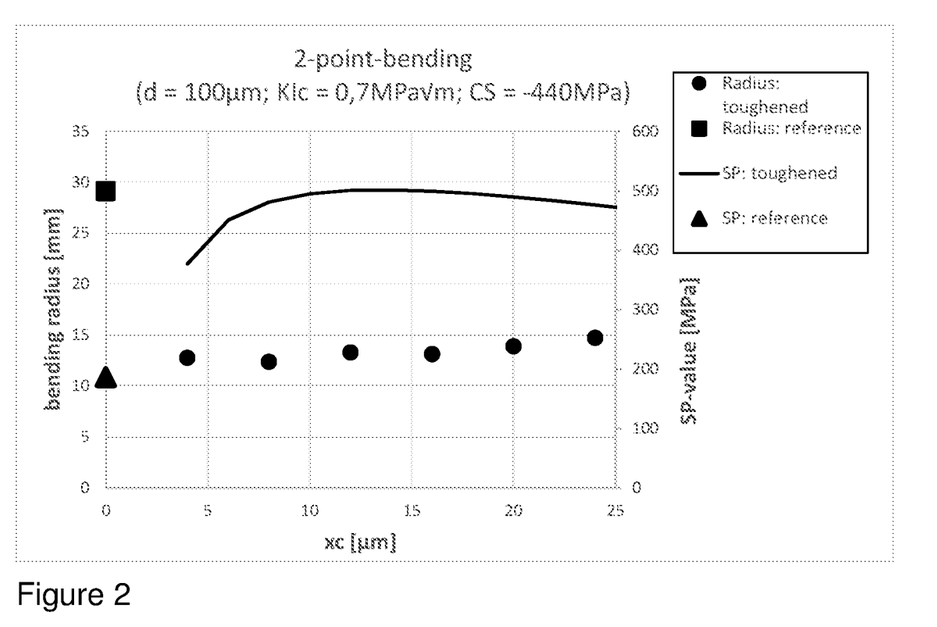
FIG. 2 illustrates the correlation between measured bending radii (characteristic value according to Weibull statistics) and the calculated SP-values (secondary y-axis) using a further exemplary glass with d=100 µm, $K_{Ic}$=0.7 MPa·√m and CS=−960 MPa; the two reference values indicate the bending radius or the SP-value of a non-toughened glass, respectively.

FIG. 2 shows a comparable diagram once more for another exemplary glass having a pre-stress of only −440 MPa (see diagram title). As can be seen, the achievable bending radii are considerably higher and the SP-graph is considerably lower as compared to the exemplary glass having CS=−960 MPa, which is illustrated in FIG. 1. Thus, lower bending radii can be achieved with higher pre-stress. These measurements were done with a stepped roll as described in DE 10 2014 110 855 A1. The bending radius in the diagram is the radius of the roll on which the glass broke.

Figure 3:
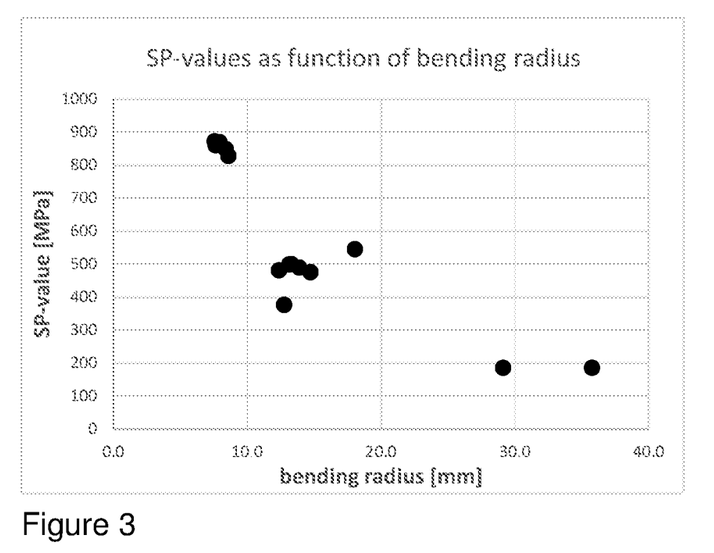
FIG. 3 illustrates SP-values depending on the bending radius; the two data points having low SP-values below 200 MPa are the reference values of a non-toughened glass.
Figure 4:
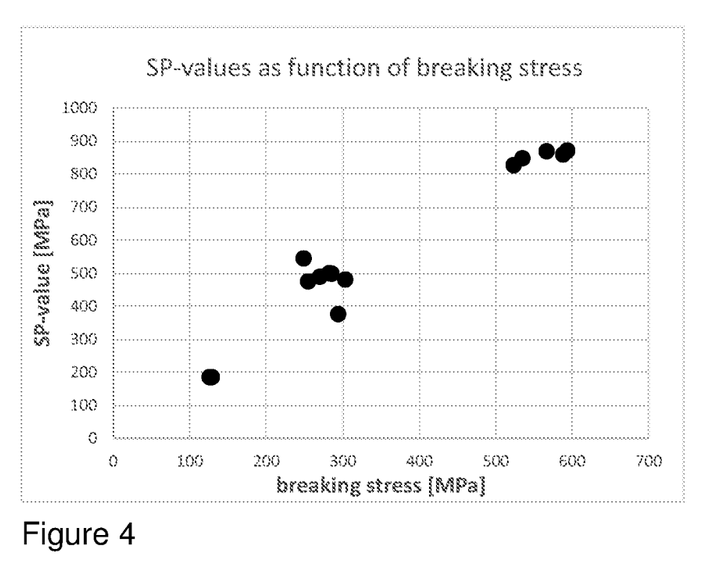
FIG. 4 illustrates SP-values depending on the breaking stress; the two data points having low SP-values below 200 MPa are the reference values of a non-toughened glass.

If the data for both exemplary glasses are shown in one diagram, this results in the two diagrams shown in FIGS. 3 and 4 having SP as a function of bending radius or as a function of breaking stress (the higher the stress, the lower the bending radius), respectively. It can be seen that lower bending radii can be achieved with higher SP-values. Higher SP-values are related with a higher breaking stress. The two data points with the low SP-values below 200 MPa are the reference values and are also representative for glasses that cannot be toughened or that have only very low CS-values.

FIGS. 5 to 9 show diagrams in which the survival parameter is shown as function of the other parameters. The x-axis is always taken by $x_c$. Two further parameters are kept fixed and the third is varied by the graphs. Which parameters are fixed with which value is indicated in the title of each diagram.

Figure 5:
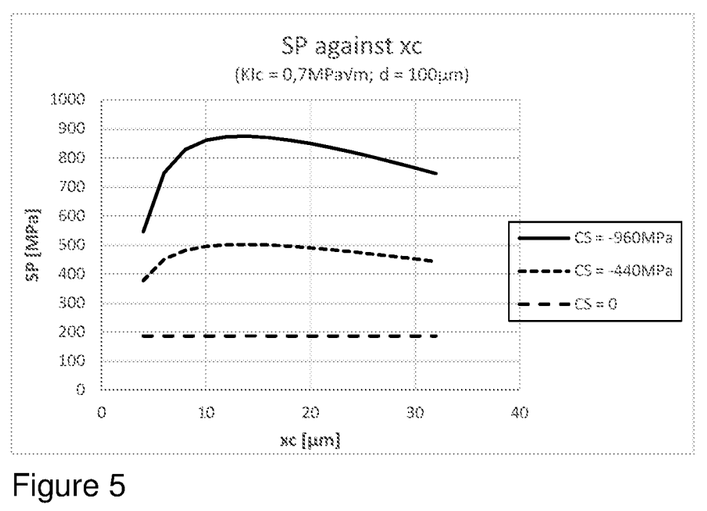
FIG. 5 illustrates SP-values depending on $x_c$ for three glasses that differ with respect to the compressive stress CS.
Figure 6:
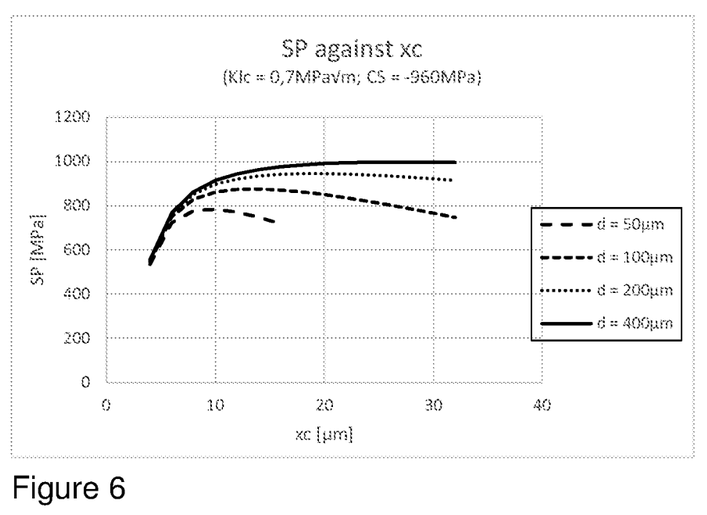
FIG. 6 illustrates SP-values depending on $x_c$ for four glasses that differ with respect to their thickness d.
Figure 7:
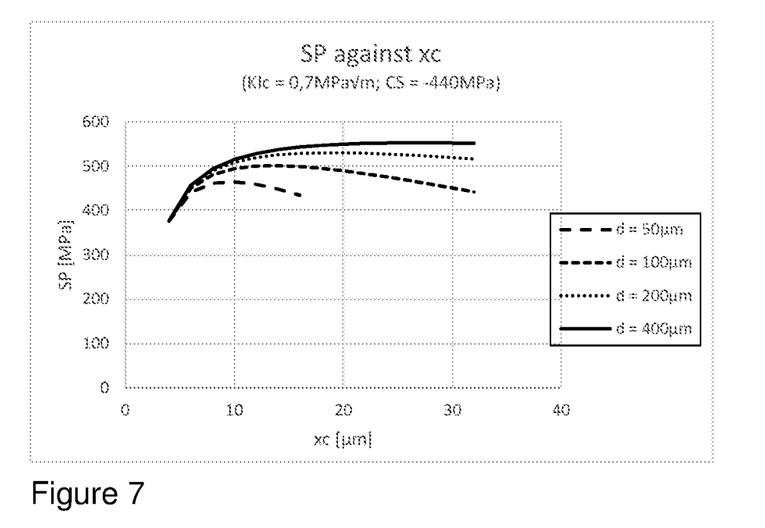
FIG. 7 illustrates SP-values depending on $x_c$ for four glasses that differ with respect to their thickness d.
Figure 8:
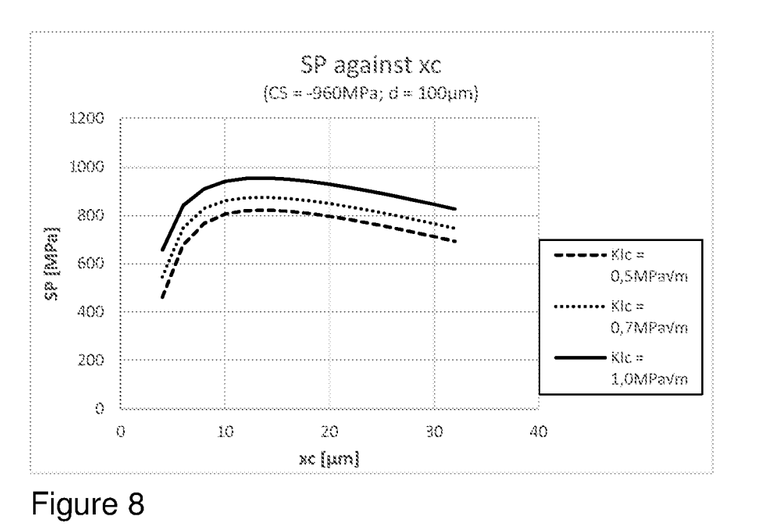
FIG. 8 illustrates SP-values depending on $x_c$ for three glasses that differ with respect to their fracture toughness $K_{Ic}$.
Figure 9:
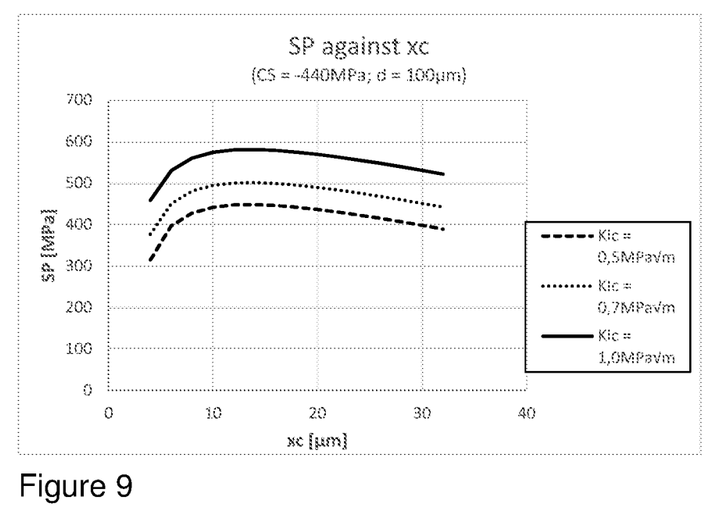
FIG. 9 illustrates SP-values depending on $x_c$ for three glasses that differ with respect to their fracture toughness $K_{Ic}$.

FIG. 5 shows that the survival parameter SP is increased at higher pre-stress CS. FIG. 6 and FIG. 7 show that a higher article thickness is correlated with higher SP-values. In FIGS. 8 and 9, it can be seen that a higher fracture toughness $K_{Ic}$ correlates with higher SP-values.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice hi the art to which this invention pertains and which fall within the limits of the appended claims.

What is claimed is:

1. A method for providing a set of articles of translucent and brittle material, comprising:
   determining a plurality of parameters for individual articles of a plurality of articles, the determined plurality of parameters of each individual article comprising a fracture toughness (KO, a compressive stress (CS), a characteristic penetration depth ($x_c$), and an article thickness (d);
   selecting a plurality of satisfactory articles from the plurality of articles, the plurality of satisfactory articles being dependent upon the plurality of parameters satisfying the following equation:

$$\frac{395 \cdot K_{Ic}}{\sqrt{m}} = SP \cdot \left(\frac{\pi}{2} - \arcsin\left(\frac{B}{4 \cdot 10^{-6} \cdot m}\right)\right) - \frac{2}{d} \cdot \sqrt{(1{,}6 \cdot 10^{-11} \cdot m^2 - B^2)} +$$
$$CS \cdot \left(\left(1 - \frac{x_c}{0{,}843 \cdot d}\right) \cdot \left(\frac{\pi}{2} - \arcsin\left(\frac{B}{4 \cdot 10^{-6} \cdot m}\right)\right)\right) -$$
$$\frac{0{,}843 \cdot \sqrt{(1{,}6 \cdot 10^{-11} \cdot m^2 - B^2)}}{x_c},$$

wherein $$B = \frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right)$$

for $$0 \le \frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right) \le 4 \cdot 10^{-6},$$

wherein $B = 0$ for $$0 > \frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right),$$

wherein $B = 0$ for $$\frac{x_c}{0{,}843} \cdot \left(\frac{d}{CS \cdot d + 2{,}37 \cdot SP \cdot x_c}\right) \cdot \left(SP + CS - \frac{CS \cdot x_c}{0{,}843 \cdot d}\right) > 4 \cdot 10^{-6},$$

wherein m=1 meter,
wherein $x_c > 0$ μm, and
wherein SP is larger than 250 MPa; and
physically separating the selected plurality of satisfactory articles from other articles of the plurality of articles.

2. The method according to claim 1, wherein the translucent and brittle material comprises a material selected from the group consisting of glass, glass ceramic, ceramic or crystals.

3. The method according to claim 1, wherein the fracture toughness $K_{Ic}$ is larger than 0.4 MPa·√m.

4. The method according to claim 1, wherein the compressive stress CS is larger than 200 MPa.

5. The method according to claim 1, wherein the characteristic penetration depth $x_c$ is at least 2 μm and at most 50 μm.

6. The method according to claim 1, wherein the article thickness d is in a range of from 5 μm to 500 μm.

7. A set of articles, consisting of:
a plurality of articles spatially combined together and each comprising a translucent and brittle material, wherein each of the plurality of articles has a fracture toughness $K_{Ic}$, a compressive stress CS, a characteristic penetration depth $x_c$ and an article thickness d, wherein the following equation is satisfied for each of the plurality of articles:

$$\frac{395 \cdot K_{Ic}}{\sqrt{m}} = SP \cdot \left(\frac{\pi}{2} - \arcsin\left(\frac{B}{4 \cdot 10^{-6} \cdot m}\right) - \frac{2}{d} \cdot \sqrt{(1.6 \cdot 10^{-11} \cdot m^2 - B^2)}\right) + CS \cdot \left(\left(1 - \frac{x_c}{0.843 \cdot d}\right) \cdot \left(\frac{\pi}{2} - \arcsin\left(\frac{B}{4 \cdot 10^{-6} \cdot m}\right)\right) - \frac{0.843 \cdot \sqrt{(1.6 \cdot 10^{-11} \cdot m^2 - B^2)}}{x_c}\right),$$

wherein $$B = \frac{x_c}{0.843} \cdot \left(\frac{d}{CS \cdot d + 2.37 \cdot SP \cdot x_c}\right) \cdot \left(SP + CS - \frac{CS \cdot x_c}{0.843 \cdot d}\right)$$

for $$0 \le \frac{x_c}{0.843} \cdot \left(\frac{d}{CS \cdot d + 2.37 \cdot SP \cdot x_c}\right) \cdot \left(SP + CS - \frac{CS \cdot x_c}{0.843 \cdot d}\right) \le 4 \cdot 10^{-6},$$

wherein $B = 0$ for $$0 > \frac{x_c}{0.843} \cdot \left(\frac{d}{CS \cdot d + 2.37 \cdot SP \cdot x_c}\right) \cdot \left(SP + CS - \frac{CS \cdot x_c}{0.843 \cdot d}\right),$$

wherein $B = 0$ for $$\frac{x_c}{0.843} \cdot \left(\frac{d}{CS \cdot d + 2.37 \cdot SP \cdot x_c}\right) \cdot \left(SP + CS - \frac{CS \cdot x_c}{0.843 \cdot d}\right) > 4 \cdot 10^{-6},$$

wherein m=1 meter,
wherein $x_c > 0$ μm, and
wherein SP is larger than 250 MPa.

8. The set of articles according to claim 7, wherein the translucent and brittle material comprises a material selected from the group consisting of glass, glass ceramic, ceramic or crystals.

9. The set of articles according to claim 7, wherein the fracture toughness $K_{Ic}$ is larger than 0.4 MPa·√m.

10. The set of articles according to claim 7, wherein the compressive stress CS is larger than 200 MPa.

11. The set of articles according to claim 7, wherein the characteristic penetration depth $x_c$ is at least 2 μm and at most 50 μm.

12. The set of articles according to claim 7, wherein the article thickness is in a range of from 5 μm to 500 μm.

13. The set of articles according to claim 7, further comprising a further material attached to at least one side of at least one of the plurality of articles to form a composite, wherein a Young's modulus of the further material is larger than 10 GPa.

* * * * *

UNITED STATES PATENT AND TRADEMARK OFFICE
CERTIFICATE OF CORRECTION

PATENT NO. : 10,718,698 B2  
APPLICATION NO. : 16/119437  
DATED : July 21, 2020  
INVENTOR(S) : Heiss-Chouquet et al.

Page 1 of 1

It is certified that error appears in the above-identified patent and that said Letters Patent is hereby corrected as shown below:

In the Specification

Column 5  
At Line 40, please delete "toughness KC,", and substitute therefore --toughness $K_{IC}$,--; and  
At Line 54, please delete "toughness K", and substitute therefore --toughness $K_{IC}$--.

Column 8  
At Line 28, please delete "10 nm", and substitute therefore --10μm--; and  
At Lines 42-43, please delete "at least 100 m.", and substitute therefore --at least 100 μm.--.

Column 9  
At Line 37, please delete "at least 500 m.", and substitute therefore --at least 500 μm.--.

In the Claims

Column 16  
At Line 18, in Claim 1, please delete "(KO, a", and substitute therefore --($K_{IC}$, a--.

Signed and Sealed this  
Thirtieth Day of November, 2021

Drew Hirshfeld  
*Performing the Functions and Duties of the*  
*Under Secretary of Commerce for Intellectual Property and*  
*Director of the United States Patent and Trademark Office*